United States Patent [19]

Averill et al.

[11] Patent Number: 4,919,679
[45] Date of Patent: Apr. 24, 1990

[54] FEMORAL STEM SURGICAL INSTRUMENT SYSTEM

[75] Inventors: Robert G. Averill, Ringwood; Alfred J. Zarnowski, North Plainfield; Matthew V. Lyons, Hoboken, all of N.J.

[73] Assignee: Osteonics Corp., Allendale, N.J.

[21] Appl. No.: 304,782

[22] Filed: Jan. 31, 1989

[51] Int. Cl.$^5$ .................. A61F 2/36; A61B 17/00; A61B 17/18

[52] U.S. Cl. ........................... 623/23; 606/62; 606/100

[58] Field of Search ............. 128/92 R, 92 K, 303 R; 623/16, 18, 20, 22, 23; 433/148, 150, 152; 254/19, 20; 29/254, 255; 81/27, 44

[56] References Cited

U.S. PATENT DOCUMENTS

| | | | |
|---|---|---|---|
| 3,843,975 | 10/1974 | Tronzo | 623/23 |
| 4,404,692 | 9/1983 | Eftekhar | 623/22 |
| 4,423,721 | 1/1984 | Otte et al. | 128/92 VT |
| 4,549,319 | 10/1985 | Meyer | 623/18 X |
| 4,834,081 | 5/1989 | Van Zile | 128/92 VT |

FOREIGN PATENT DOCUMENTS 2615097 11/1988 France ................ 128/92 VT

Primary Examiner—Richard J. Apley
Assistant Examiner—David J. Bender
Attorney, Agent, or Firm—Samuelson & Jacob

[57] ABSTRACT

A femoral stem surgical instrument system includes a handle component and an impact component, either one of which is selectively coupled with a femoral stem through a recess in the femoral stem, the recess providing separate facilities for the appropriate coupling of either of the components with the femoral stem, with each of the separate facilities being protected against damage when the other of the facilities is in use.

15 Claims, 2 Drawing Sheets

FEMORAL STEM SURGICAL INSTRUMENT SYSTEM

BACKGROUND OF THE INVENTION

The present invention relates generally to surgical instruments and pertains, more specifically, to surgical instruments used in connection with the implant and subsequent removal of prosthetic joints.

The use of prosthetic implants to replace the natural joints of the body, either as a result of disease or injury to the natural joint, is becoming more and more commonplace. For example, in the replacement of a hip joint, it is very often necessary to replace the natural femoral head with a prosthetic femoral stem which enters the femur and provides an accurately located and securely held prosthetic head in place of the natural femoral head. The procedures for implanting a femoral stem usually include coupling of the femoral stem with instruments which enable the surgeon to manipulate the femoral stem for appropriate positioning during implant, for impacting the femoral stem during implant or during extraction, and for subsequent extraction of the femoral stem, should such extraction become necessary.

SUMMARY OF THE INVENTION

The present invention provides a surgical instrument system having components which are adapted readily to the existing structure of current femoral stems for enhancing the ability of the surgeon to manipulate a femoral stem during implant and extraction and exhibits several objects and advantages, some of which may be summarized as follows: enables use in connection with currently available femoral stem configurations for a wider range of operating procedures, such as direct manipulation of the femoral stem for proper orientation and location during implant, impacting of the femoral stem during implant or extraction of the femoral stem, and pulling upon the femoral stem during extraction; provides exceptional simplicity in design, construction and use; provides secure coupling of the femoral stem with a component of the instrument system which enables a wider range of manipulations, including rotational movements such as those often performed interoperatively in testing the ability of the implant to withstand torsional loads; exhibits compact, yet effective components for ease of use within the confines of the limited operating space available to the surgeon during the implant procedure; provides facilities for selectively coupling either one of more than one instrument component alternately at the same location on a femoral stem while protecting against damage to one facility when using the other; complies with all of the requirements for surgical instruments insofar as construction and materials necessary to serve the surgical environment; and provides rugged construction for reliable service over an extended service life.

The above objects and advantages, as well as further objects and advantages, are attained by the present invention which may be described briefly as the improvement in a femoral stem surgical instrument system for use in connection with manipulating, impacting and extracting a femoral stem during procedure involving the placement of the femoral stem relative to a femur, the femoral stem extending in an axial direction and including a proximal surface transverse to the longitudinal direction and making an acute angle with the longitudinal direction, and a recess extending in the axial direction from the proximal surface distally into the femoral stem, the femoral stem surgical instrument system including a handle component having a coupling projection for selective engagement with the recess to couple the handle component with the femoral stem for manipulation of the femoral stem in direct response to manipulation of the handle component, and an impact component having an impact pin for selective reception in the recess for selectively impacting the femoral stem, the improvement comprising: a first bore portion extending in an axial direction along the recess and having a first diameter, the first bore portion being spaced distally from the proximal surface and including a first coupling configuration therein; a second bore portion extending in an axial direction from the proximal surface toward the first bore portion and having a second diameter larger than the first diameter; a third bore portion extending in an axial direction between the first bore portion and the second bore portion and having a third diameter smaller then the second diameter and no smaller than the first diameter; and a transverse shoulder within the recess between the second bore portion and the third bore portion; the coupling projection including a second coupling configuration complementary to the first coupling configuration; the handle component including a coupling sleeve carried by the handle component for relative movement between the coupling sleeve and the coupling projection in axial directions, a coupling surface on the coupling sleeve, the coupling surface making an acute angle with the axial direction for matching the acute angle of the proximal surface so as to enable selective coupling of the coupling surface with the proximal surface, and locking means on the handle component for locking the coupling sleeve against axial movement relative to the proximal surface of the femoral stem when the first and second coupling configurations are coupled together and the coupling surface is in engagement with the proximal surface of the femoral stem; the impact pin having a diameter complementary to the diameter of the second bore portion, and an impact shoulder complementary to the transverse shoulder within the recess for engagement of the impact pin with the transverse shoulder upon engagement of the impact component with the femoral stem.

The invention will be more fully understood, while still further objects and advantages will become apparent, in the following detailed description of a preferred embodiment illustrated in the accompanying drawing, in which:

DESCRIPTION OF THE PREFERRED EMBODIMENT

Figure 1:
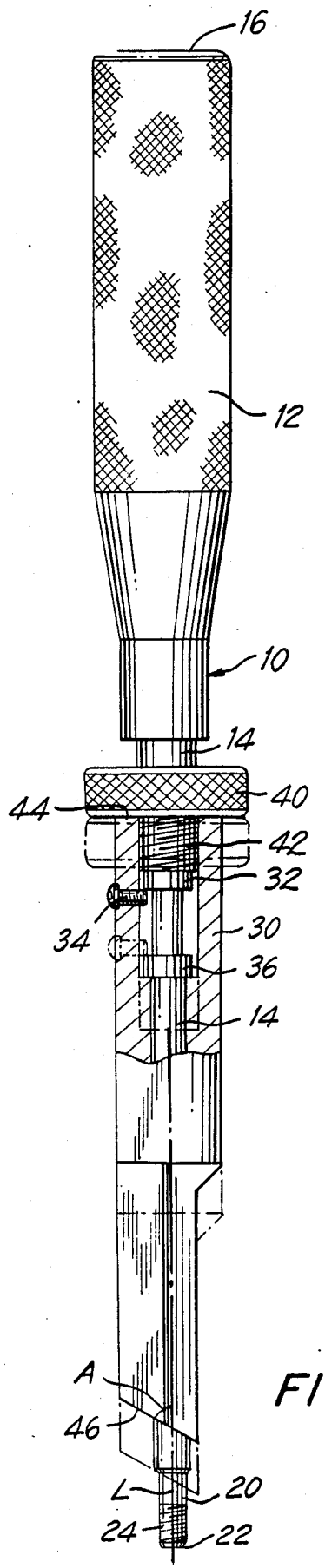
FIG. 1 is a longitudinal elevational view, partially cross-sectioned, of a component of the system of the present invention.

Referring now to the drawing, and especially to FIG. 1 thereof, the surgical instrument system of the present invention includes a handle component 10 having a manipulating handle 12 affixed to a central shaft 14 adjacent one end 16 of the handle component 10. A coupling projection 20 is integral with the central shaft 14, at the opposite end 22 of the handle component 10, extends axially along the longitudinal axis L of the central shaft 14 and includes a coupling configuration in the form of a screw thread 24.

A coupling sleeve 30 is mounted for sliding movement along the central shaft 14 between a retracted position, shown in full lines, and an advanced position, shown in phantom. An upper stop ring 32 is affixed to the central shaft 14 and is abutted by a stop screw 34 carried by the coupling sleeve 30, when the coupling sleeve 30 is located in the retracted position, and a lower stop ring 36 is affixed to the central shaft 14 and is abutted by the stop screw 34 when the coupling sleeve 30 is located in the advanced position. In this manner, the coupling sleeve 30 is captured on the central shaft 14 and movement of the coupling sleeve 30 relative to the central shaft 14 is confined to axial movement between the retracted and the advanced positions. A locking collar 40 is threaded onto the central shaft 14 at threads 42 in the central shaft 14 and is selectively movable axially along the threads 42 adjacent a locking surface 44 on one end of the coupling sleeve 30 to provide locking means for locking the coupling sleeve 30 against axial movement along the central shaft 14, as will be explained below in connection with FIG. 2. A coupling surface 46 is located at the other end of the coupling sleeve 30. Coupling surface 46 is essentially planar, extends transversely across the coupling sleeve 30 and makes and acute angle A with the longitudinal axis L.

Figure 2:
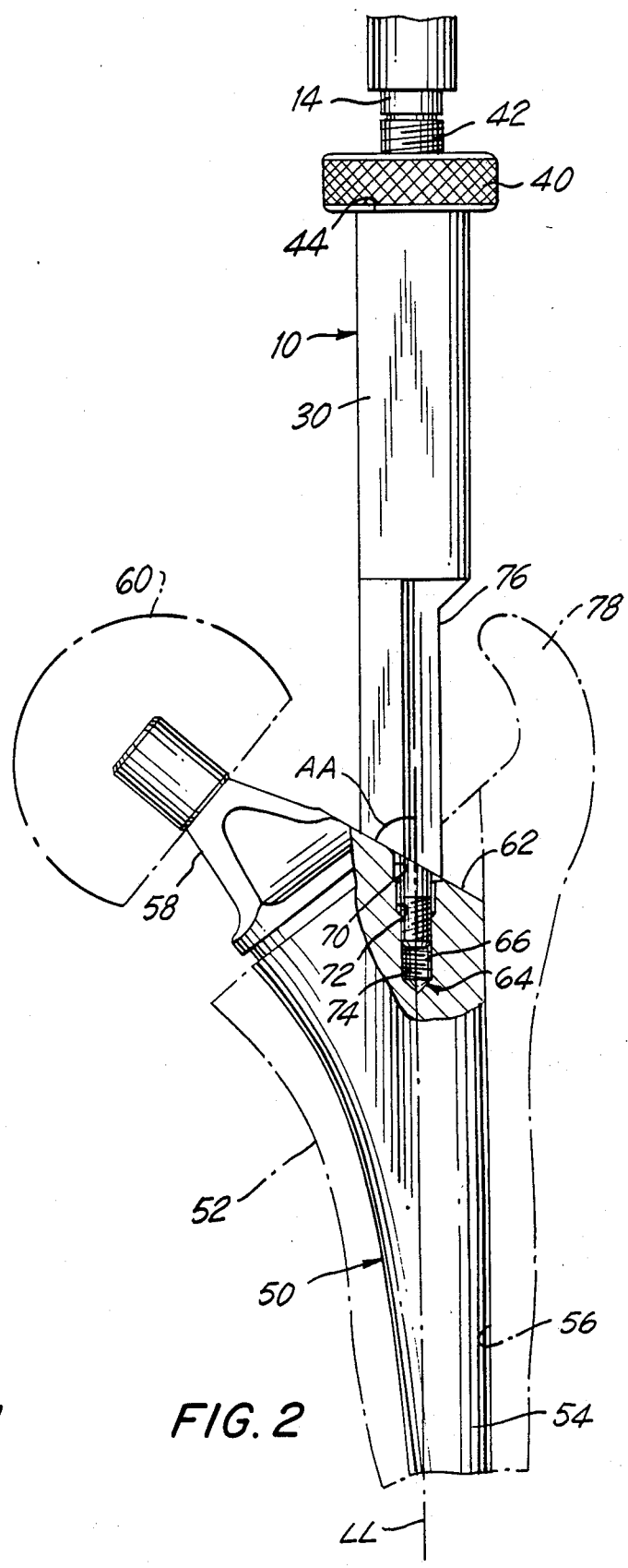
FIG. 2 is a longitudinal fragmentary view of the component of FIG. 1 coupled with a femoral stem.

Turning now to FIG. 2, a femoral stem 50 is shown coupled to the handle component 10 for manipulation of the femoral stem 50 during implant of the femoral stem 50 into a femur, shown in phantom at 52. Femoral stem 50 extends axially, along a longitudinal axis LL, and includes a stem portion 54 for reception within a prepared cavity 56 in the femur 52, and a post 58, upon which post 58 a prosthetic femoral head will be located, as shown in phantom at 60. An essentially planar proximal surface 62 extends transversely across the femoral stem 50 and makes an acute angle AA with the longitudinal axis LL.

Figure 3:
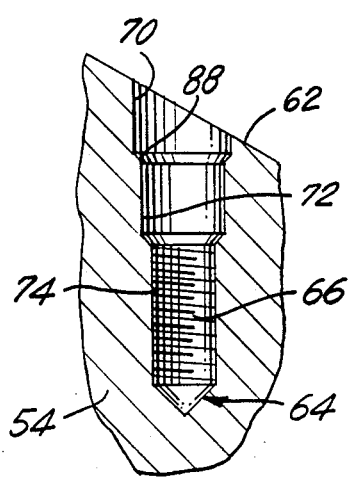
FIG. 3 is an enlarged fragmentary cross-sectional view of a portion of the femoral stem.

A recess 64, illustrated in an enlarged fragmentary form in FIG. 3, extends in an axial direction from the proximal surface 62 distally into the femoral stem 50 and includes a first bore portion 66 spaced distally from the proximal surface 62. A second bore portion 70 extends axially from the proximal surface 62 toward the first bore portion 66, and a third bore portion 72 extends axially between the first bore portion 66 and the second bore portion 70. First bore portion 66 has a coupling configuration in the form of a screw thread 74 extending along the inner surface of the bore portion 66. The inner diameter of the second bore portion 70 is larger than the inner diameter of the first bore portion 66, and the inner diameter of the third bore portion 72 is smaller than the inner diameter of the second bore portion 70, but no smaller, and preferably somewhat larger, than the inner diameter of the first bore portion 66.

The handle component 10 is coupled with the femoral stem 50 by first threading the screw thread 24 of the coupling projection 20 into the screw thread 74 of the first bore portion 66, while the coupling sleeve 30 is in the retracted position. Then, the coupling sleeve 30 is advanced along the central shaft 14, toward the advanced position, until the coupling surface 46 abuts the proximal surface 64 of the femoral stem 50. Angle A is equal to angle AA so that the surfaces 46 and 62 match and engage one another as depicted in FIG. 2. Once the coupling surface 46 is seated upon the proximal surface 64, the locking collar 40 is advanced along the threads 42 of the central shaft 14, against the locking surface 44 of the coupling sleeve 30, thereby forcing the coupling sleeve 30 into rigid coupled engagement with the femoral stem 50. The coupling sleeve 30 includes a relief notch 76 along the side of the coupling sleeve 30 which confronts the greater trochanter 78 of the femur 52 so as to assure that the coupling sleeve 30 clears the greater trochanter 78. The combination of the angled surfaces 46 and 62 and the locking forces exerted by the locking collar 40 upon the coupled angled surfaces 46 and 62 establishes a coupling between the handle component 10 and the femoral stem 50 which resists relative movement between the handle component 10 and the femoral stem 50, thereby enabling manipulation of the femoral stem 50 in direct response to manipulation of the handle component 10. Not only does the coupling arrangement resist relative axial movements between the femoral stem 50 and the handle component 10, but the angled surfaces 46 and 62 assure that the femoral stem 50 will not turn relative to the handle component 10 upon the exertion of torsional forces upon the femoral stem 50. Release of the handle component 10 from the femoral stem 50 is accomplished with ease by merely backing off the locking collar 40, retracting the coupling sleeve 30, and then disengaging the threaded connection between the coupling projection 20 and the first bore portion 66 of the recess 64. Preferably, coupling projection 20 is constructed of a biocompatible material so that in the event any minute particles of the coupling projection 20 remain behind in the recess 64, no deleterious effects will result.

Figure 4:
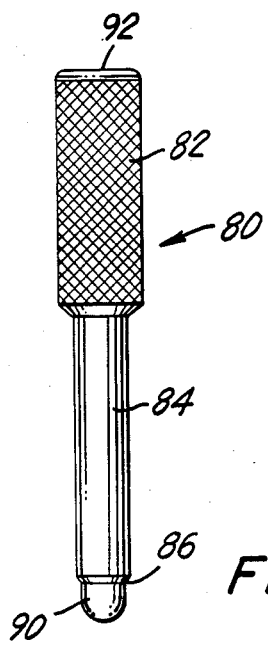
FIG. 4 is a longitudinal elevational view of another component of the system.
Figure 5:
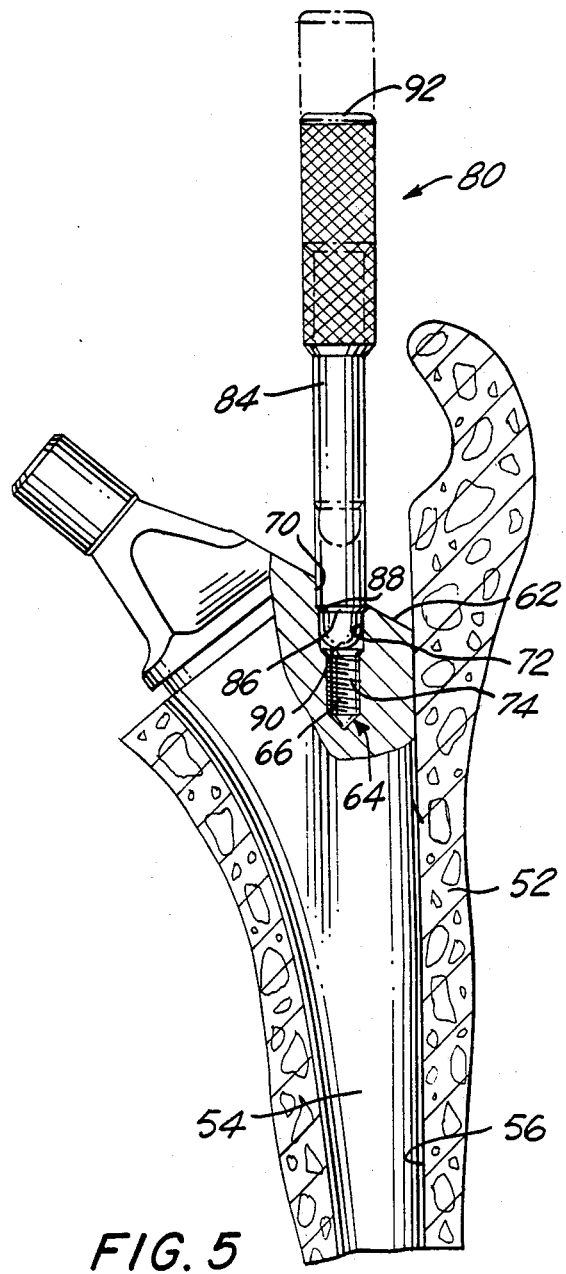
FIG. 5 is a longitudinal fragmentary view of the component of FIG. 4 coupled with the femoral stem.

Referring now to FIG. 4, an impact component of the femoral stem surgical instrument system is shown at 80 and is seen to have a handgrip 82 and an impact pin 84 integral with the handgrip 82 and projecting axially from the handgrip 82. Impact pin 84 has a outer diameter complementary to the second bore portion 70 of the recess 64 in the femoral stem 50 and, as best seen in FIG. 5, is selectively received within the second bore portion 70 of the recess 64. Thus, as seen in phantom, the impact component 80 is aligned with the recess 64 and then is advanced so that the impact pin 84 enters the second bore portion 70 of the recess 64. Advancement is continued until an impact shoulder 86 on the impact pin 84 is seated against a complementary transverse shoulder 88 in the recess 64, located between the second bore portion 70 and the third bore portion 72, as shown in full lines. A pilot portion 90 on the impact pin 84 projects axially beyond the impact shoulder 86 and has an outer diameter smaller than the diameter of the impact pin 84. Pilot portion 90 serves to guide the impact pin 84 into the recess 64 and assists in locating the impact shoulder 86 properly in abutment with the transverse shoulder 88 of the recess 64. Once the impact pin 84 is fully engaged within the recess 64, as shown in full lines in FIG. 5, the pilot portion 90 enters the third bore portion 72. Impact forces then can be applied to the impact component 80, as by striking the upper end 92 of the impact component 80, and the impact forces will be transmitted to the femoral stem 50 through the engaged shoulders 86 and 88. Since the engaged shoulders 86 and 88 are spaced axially away from the threaded first bore portion 66, damage to the threaded first bore portion 66 will be avoided and the integrity of the threaded connection provided by the threaded first bore portion 66 will be maintained for subsequent selective engagement and attachment of the handle component 10, should it be necessary to extract or otherwise manipulate the femoral stem 50 subsequent to impacting the femoral stem with the impact component 80. Likewise, the arrangement of the several bore portions in recess 64 assures that the transverse shoulder 88 will be protected against damage when the coupling projection 20 is engaged within the first bore portion 66 so that the integrity of the second bore portion 70 and the transverse shoulder 88 will remain intact for the selective use of the impact component 80, unaffected by the use of the handle component 10. In this manner, recess 64 provides separate coupling facilities in a compact and effective manner, without the likelihood of damage to either coupling arrangement as a result of using the other coupling arrangement.

Both the handle component 10 and the impact component 80 are constructed of a minimum number of parts of simple design and configuration. All of the parts of each component are manufactured readily of materials which can withstand the rigors of use, including both the conditions encountered during employment in the procedures for which the components are designed and those encountered during cleaning, storage and handling. The components are easily put into use and simplify the procedures followed by the surgeon, thereby benefiting the patient.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. The improvement in a femoral stem surgical instrument system for use in connection with manipulating, impacting and extracting a femoral stem during procedures involving the placement of the femoral stem relative to a femur, the femoral stem extending in an axial direction and including a proximal surface transverse to the longitudinal direction and making an acute angle with the longitudinal direction, and a recess extending in the axial direction from the proximal surface distally into the femoral stem, the femoral stem surgical instrument system including a handle component having a coupling projection for selective engagement with the recess to couple the handle component with the femoral stem for manipulation of the femoral stem in direct response to manipulation of the handle component, and an impact component having an impact pin for selective reception in the recess for selectively impacting the femoral stem, the improvement comprising:
   a first bore portion extending in an axial direction along the recess and having a first diameter, the first bore portion being spaced distally from the proximal surface and including a first coupling configuration therein;
   a second bore portion extending in an axial direction from the proximal surface toward the first bore portion and having a second diameter larger than the first diameter;
   a third bore portion extending in an axial direction between the first bore portion and the second bore portion and having a third diameter smaller then the second diameter and no smaller than the first diameter; and
   a transverse shoulder within the recess between the second bore portion and the third bore portion;
   the coupling projection including a second coupling configuration complementary to the first coupling configuration;
   the handle component including a coupling sleeve carried by the handle component for relative movement between the coupling sleeve and the coupling projection in axial directions, a coupling surface on the coupling sleeve, the coupling surface making an acute angle with the axial direction for matching the acute angle of the proximal surface so as to enable selective coupling of the coupling surface with the proximal surface, and locking means on the handle component for locking the coupling sleeve against axial movement relative to the proximal surface of the femoral stem when the first and second coupling configurations are coupled together and the coupling surface is in engagement with the proximal surface of the femoral stem;
   the impact pin having a diameter complementary to the diameter of the second bore portion, and an impact shoulder complementary to the transverse shoulder within the recess for engagement of the impact pin with the transverse shoulder upon engagement of the impact component with the femoral stem.

2. The improvement of claim 1 wherein the first and second coupling configurations comprise complementary threaded surfaces.

3. The improvement of claim 1 wherein the impact pin includes a pilot portion projecting beyond the impact shoulder for guiding the impact pin into the recess and the impact shoulder toward the transverse shoulder, the pilot portion entering the third bore portion when the impact pin is placed properly within the recess and the impact shoulder is brought into appropriate abutment with the transverse shoulder.

4. The improvement of claim 3 wherein the diameter of the third bore portion is greater than the diameter of the first bore portion.

5. The improvement of claim 1 wherein the locking means includes a locking collar on the handle component, the locking collar being movable relative to the coupling sleeve to abut the coupling sleeve when the coupling surface is in coupling engagement with the proximal surface of the femoral stem.

6. The improvement of claim 5 including a threaded connection between the locking collar and the handle component.

7. The improvement of claim 1 wherein the coupling sleeve includes a relief notch along the coupling sleeve and confronting the greater trochanter of the femur when the femoral stem is located in the femur.

8. The improvement of claim 1 wherein the coupling projection is constructed of a biocompatible material.

9. The improvement in a femoral stem surgical instrument system for use in connection with manipulating, impacting and extracting a femoral stem during procedures involving the placement of the femoral stem relative to a femur, the femoral stem extending in an axial direction and including a proximal surface transverse to the longitudinal direction and making an acute angle with the longitudinal direction, and a recess extending in the axial direction from the proximal surface distally into the femoral stem, the femoral stem surgical instrument system including a handle component having a coupling projection for selective engagement with the recess to couple the handle component with the femoral stem for manipulation of the femoral stem in direct response to manipulation of the handle component, the improvement comprising:

a bore portion extending in an axial direction along the recess, the bore portion being spaced distally from the proximal surface and including a first coupling configuration therein;

the coupling projection including a second coupling configuration complementary t the first coupling configuration;

the handle component including a coupling sleeve carried by the handle component for relative movement between the coupling sleeve and the coupling projection in axial directions, a coupling surface on the coupling sleeve, the coupling surface making an acute angle with the axial direction for matching the acute angle of the proximal surface so as to enable selective coupling of the coupling surface with the proximal surface, and locking means on the handle component for locking the coupling sleeve against axial movement relative to the proximal surface of the femoral stem when the first and second coupling configurations are coupled together and the coupling surface is in engagement with the proximal surface of the femoral stem.

10. The improvement of claim 9 wherein the first and second coupling configurations comprise complementary threaded surfaces.

11. The improvement of claim 9 wherein the locking means includes a locking collar on the handle component, the locking collar being movable relative to the coupling sleeve to abut the coupling sleeve when the coupling surface is in coupling engagement with the proximal surface of the femoral stem.

12. The improvement of claim 11 wherein the first and second coupling configurations comprise complementary threaded surfaces.

13. The improvement of claim 12 including a threaded connection between the locking collar and the handle component.

14. The improvement of claim 9 wherein the coupling sleeve includes a relief notch along the coupling sleeve and confronting the greater trochanter of the femur when the femoral stem is located in the femur.

15. The improvement of claim 9 wherein the coupling projection is constructed of a biocompatible material.

* * * * *